(12) United States Patent
Zhang et al.

(10) Patent No.: US 10,810,735 B2
(45) Date of Patent: Oct. 20, 2020

(54) METHOD AND APPARATUS FOR ANALYZING MEDICAL IMAGE

(71) Applicant: Baidu Online Network Technology (Beijing) Co., Ltd., Beijing (CN)

(72) Inventors: Shaoting Zhang, Beijing (CN); Qi Duan, Beijing (CN)

(73) Assignee: Baidu Online Network Technology (Beijing) Co., Ltd., Beijing (CN)

( * ) Notice: Subject to any disclaimer, the term of this patent is extended or adjusted under 35 U.S.C. 154(b) by 168 days.

(21) Appl. No.: 16/050,667

(22) Filed: Jul. 31, 2018

(65) Prior Publication Data
US 2019/0102878 A1 Apr. 4, 2019

(30) Foreign Application Priority Data
Sep. 30, 2017 (CN) .......................... 2017 1 0918520

(51) Int. Cl.
*G06K 9/00* (2006.01)
*G06T 7/00* (2017.01)
(Continued)

(52) U.S. Cl.
CPC ......... *G06T 7/0012* (2013.01); *G06N 3/0427* (2013.01); *G06N 3/0454* (2013.01);
(Continued)

(58) Field of Classification Search
CPC . G06T 2207/20016; G06T 2207/20084; G06T 2207/10; G06T 2207/30004;
(Continued)

(56) References Cited

U.S. PATENT DOCUMENTS

| 7,098,382 B1 * | 8/2006 | Takatsuji ........... C12N 15/8233 800/287 |
| 2007/0104094 A1 * | 5/2007 | Hischke ................ H04L 47/745 370/228 |

(Continued)

FOREIGN PATENT DOCUMENTS

| CN | 104700118 | * | 6/2015 | ............... G06K 9/46 |
| CN | 104700118 A | | 6/2015 | |

(Continued)

OTHER PUBLICATIONS

Abhinav et al, "Training Region-based Object Detectors with Online Hard Example Mining", 2016 IEEE Conference on Computer Vision and Pattern Recognition (Year: 2016).*

(Continued)

*Primary Examiner* — Amara Abdi
(74) *Attorney, Agent, or Firm* — Knobbe, Martens, Olson & Bear, LLP

(57) ABSTRACT

The present disclosure discloses a method and apparatus for analyzing medical image. A specific embodiment of the method includes: acquiring medical image data; generating multi-scale decision sample data based on the medical image data; inputting the multi-scale decision sample data into a deep neural network model to obtain an auxiliary diagnosis data of the medical image, the deep neural network model being trained according to a consistency principle between multi-scale training sample data and an output result of the deep neural network model. In the embodiment, a multi-scale training sample is used to accelerate the training process of the deep neural network model, thus the auxiliary diagnosis decision process can be accelerated, while the accuracy of the trained deep neural network model of the embodiment is improved according to a consistency principle of data between different scales and output results, (Continued)

thereby improving the accuracy of auxiliary diagnosis decision.

13 Claims, 3 Drawing Sheets

(51) Int. Cl.
  *G06T 7/136*    (2017.01)
  *G16H 30/40*    (2018.01)
  *G06N 3/08*     (2006.01)
  *G06N 3/04*     (2006.01)
  *G16H 50/20*    (2018.01)
  *G16H 50/70*    (2018.01)

(52) U.S. Cl.
  CPC ............. *G06N 3/084* (2013.01); *G06T 7/136* (2017.01); *G16H 30/40* (2018.01); *G16H 50/20* (2018.01); *G16H 50/70* (2018.01); *G06T 2207/10* (2013.01); *G06T 2207/20016* (2013.01); *G06T 2207/20081* (2013.01); *G06T 2207/20084* (2013.01); *G06T 2207/30004* (2013.01)

(58) Field of Classification Search
  CPC ......... G06T 2207/20081; G06T 7/0012; G06T 7/136; G06N 3/084; G06N 3/0454; G06N 3/0427; G06N 3/02; G16H 50/20; G16H 50/70; G16H 30/40
  See application file for complete search history.

(56) References Cited

U.S. PATENT DOCUMENTS

| | | | |
|---|---|---|---|
| 2011/0142316 A1* | 6/2011 | Wang | G06T 11/006 382/131 |
| 2013/0182096 A1* | 7/2013 | Boccara | A61B 5/0068 348/79 |
| 2014/0012558 A1* | 1/2014 | Mansi | G16H 50/50 703/11 |
| 2015/0278642 A1* | 10/2015 | Chertok | G06K 7/1482 382/156 |
| 2017/0200274 A1* | 7/2017 | Tan | G06K 9/6277 |
| 2017/0337682 A1* | 11/2017 | Liao | G06T 7/30 |
| 2017/0357844 A1* | 12/2017 | Comaniciu | G06K 9/00127 |
| 2018/0276278 A1* | 9/2018 | Cagan | G06N 5/046 |

FOREIGN PATENT DOCUMENTS

| | | |
|---|---|---|
| CN | 105551036 A | 5/2016 |
| CN | 107016665 A | 8/2017 |

OTHER PUBLICATIONS

Shrivastava et al. "Training Region-Based Object Detectors with Online Hard Example Mining," Jul. 7, 2016 in 5 pages.

* cited by examiner

METHOD AND APPARATUS FOR ANALYZING MEDICAL IMAGE

CROSS-REFERENCE TO RELATED APPLICATIONS

This application claims priority to Chinese Application No. 201710918520.4, filed with the State Intellectual Property Office of the People's Republic of China (SIPO) on Sep. 30, 2017, the content of which is incorporated herein by reference in its entirety.

TECHNICAL FIELD

Embodiments of the present disclosure relate to the field of computer technology, specifically relate to the field of computer network technology, and more specifically relate to a method and apparatus for analyzing medical image.

BACKGROUND

At present, most techniques for diagnosing a full-field pathological image are based on a sliding window classification model, that is, all positions in the full-field image are traversed using a sliding window with a fixed size, then lesion/non-lesion areas in an image in each sliding window are classified and identified, and finally a comprehensive diagnosis on all the diagnosis results is performed. A classification network often uses popular classification network models in the field of deep learning, such as VGG16, ResNet, or Inception.

In the techniques for diagnosing the full-field pathological image, since the resolution of the full-field image is very high, each full-field pathological image will generate large amount of sliding window sample data based on traversals.

SUMMARY

The objective of some embodiments of the present disclosure is to provide a method and apparatus for analyzing a medical image.

In a first aspect, some embodiments of the present disclosure provide a method for analyzing a medical image, the method including: acquiring medical image data; generating multi-scale decision sample data based on the medical image data; and inputting the multi-scale decision sample data into a depth neural network model to obtain an auxiliary diagnosis data of the medical image, the depth neural network model being trained according to a consistency principle between multi-scale training sample data and an output result of the deep neural network model.

In some embodiments, the deep neural network model is trained by: acquiring full-field pathological image data; generating multi-scale training sample data based on the full-field pathological image data; and training the deep neural network model according to a consistency principle between data and an output result of the deep neural network model using the multi-scale training sample data.

In some embodiments, the generating the multi-scale training sample data based on the full-field pathological image data includes: removing a non-effective pathological tissue area in the full-field pathological image data to obtain an effective pathological tissue area; and generating the multi-scale training sample data based on the effective pathological tissue area.

In some embodiments, the generating the multi-scale training sample data based on the full-field pathological image data includes: determining a positional correspondence relationship between the multi-scale training sample data using a multi-scale alignment algorithm.

In some embodiments, the training the deep neural network model using the multi-scale training sample data includes: training the deep neural network model respectively using training sample data of different scales in the multi-scale training sample data; or training the deep neural network model jointly using the training sample data of different scales in the multi-scale training sample data.

In some embodiments, the training the deep neural network model using the multi-scale training sample data includes: establishing a connection between training sample data of different scales in the multi-scale training sample data using topology or dynamic coding; and training the deep neural network model based on the connection between the training sample data of different scales.

In some embodiments, the training the deep neural network model using the multi-scale training sample data includes at least one of: selecting sample data with a score lower than a predetermined threshold from the multi-scale training sample data for back propagation, to update parameters of the deep neural network model; or selecting sample data expired in at least one of training or detection from the multi-scale training sample data for hard example mining, to update parameters of the deep neural network model.

In some embodiments, the deep neural network model includes one or more of disease classification, disease area detection, or disease area segmentation.

In a second aspect, some embodiments of the present disclosure provide an apparatus for analyzing a medical image, the apparatus including: a medical image acquiring unit, configured to acquire medical image data; a decision sample generating unit, configured to generate multi-scale decision sample data based on the medical image data; and a medical image analyzing unit, configured to input the multi-scale decision sample data into a deep neural network model to obtain an auxiliary diagnosis data of the medical image, the deep neural network model being trained according to a consistency principle between multi-scale training sample data and an output result of the deep neural network model.

In some embodiments, the deep neural network model in the medical image analyzing unit is trained based on following units: a pathological image acquiring unit, configured to acquire full-field pathological image data; a training sample generating unit, configured to generate multi-scale training sample data based on the full-field pathological image data; and a neural network training unit, configured to train the deep neural network model according to a consistency principle between data and an output result of the deep neural network model using the multi-scale training sample data.

In some embodiments, the sample data generating unit includes: a pathological area determining unit, configured to remove a non-effective pathological tissue area in the full-field pathological image data to obtain an effective pathological tissue area; and a lesion sample generating unit, configured to generate the multi-scale training sample data based on the effective pathological tissue area.

In some embodiments, the sample data generating unit is further configured to: determine a positional correspondence relationship between the multi-scale training sample data using a multi-scale alignment algorithm.

In some embodiments, the sample data generating unit is further configured to: train the deep neural network model respectively using training sample data of different scales in the multi-scale training sample data; or train the deep neural network model jointly using the training sample data of different scales in the multi-scale training sample data.

In some embodiments, the sample data generating unit is further configured to: establish a connection between training sample data of different scales in the multi-scale training sample data using topology or dynamic coding; and train the deep neural network model based on the connection between the training sample data of different scales.

In some embodiments, the neural network training unit is further configured to at least one of: select sample data with a score lower than a predetermined threshold from the multi-scale training sample data for back propagation, to update parameters of the deep neural network model; or select sample data expired in at least one of training or detection from the multi-scale training sample data for hard example mining, to update parameters of the deep neural network model.

In some embodiments, the deep neural network model in the neural network training unit comprises one or more of disease classification, disease area detection, or disease area segmentation.

In a third aspect, some embodiments of the present disclosure provide a device, including: one or more processors; and a storage apparatus, configured to store one or more programs; wherein the one or more programs, when executed by the one or more processors, cause the one or more processors to implement the method for analyzing a medical image described in any one of the above embodiments.

In a fourth aspect, some embodiments of the present disclosure provide a computer readable storage medium, storing a computer program thereon, wherein the computer program, when executed by a processor, implements the method for analyzing a medical image described in any one of the above embodiments.

In the method and apparatus for analyzing a medical image according to some embodiments of the present disclosure, first medical image data is acquired, then multi-scale decision sample data is generated based on the medical image data, finally the multi-scale decision sample data is input into a deep neural network model to obtain an auxiliary diagnosis data of the medical image, the deep neural network model being trained according to a consistency principle between data and an output result using multi-scale training sample data. In some embodiments, a multi-scale training sample of a full-field pathological sample can be acquired, and the multi-scale training sample is used to accelerate the training process of the deep neural network model, thus the auxiliary diagnosis decision process of the multi-scale decision sample can be accelerated. At the same time, in some embodiments, the accuracy of the trained deep neural network model is improved based on a consistency principle between data of different scales and output results, thereby the accuracy of auxiliary diagnosis decision is improved.

BRIEF DESCRIPTION OF THE DRAWINGS

After reading detailed descriptions of non-limiting embodiments with reference to the following accompanying drawings, other features, objectives and advantages of the present disclosure will be more apparent.

DETAILED DESCRIPTION OF EMBODIMENTS

The present disclosure will be further described below in detail in combination with the accompanying drawings and the embodiments. It should be appreciated that the specific embodiments described herein are merely used for explaining the relevant disclosure, rather than limiting the disclosure. In addition, it should be noted that, for the ease of description, only the parts related to the relevant disclosure are shown in the accompanying drawings.

It should also be noted that the embodiments in the present disclosure and the features in the embodiments may be combined with each other on a non-conflict basis. The present disclosure will be described below in detail with reference to the accompanying drawings and in combination with the embodiments.

Figure 1:
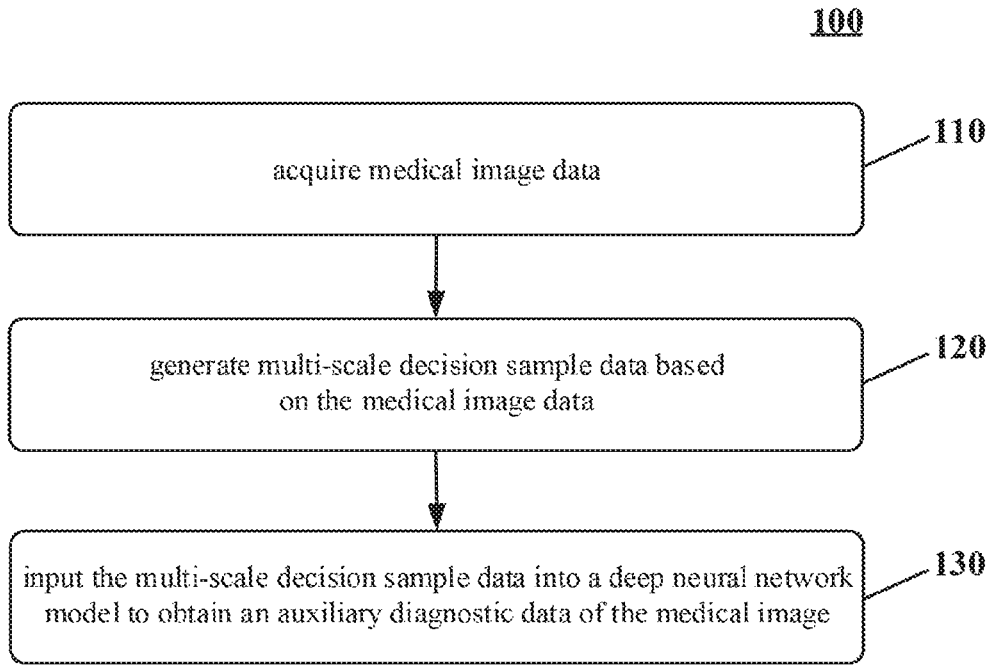
FIG. 1 is a schematic flowchart of an embodiment of a method for analyzing a medical image according to the present disclosure.

FIG. 1 illustrates a flow 100 of an embodiment of a method for analyzing a medical image according to some embodiments of the present disclosure. The method for analyzing a medical image includes:

Step 110, acquiring medical image data.

In some embodiments, the medical image data refers to all kinds of high-dimensional or large-scale medical image data. The high-dimensional image here refers to a two-dimensional image (such as a pathological image, or a X-ray image), a three-dimensional image (such as CT, MRI, or PET), or a four-dimensional image (multi-temporal CT varying with time, with a time dimension added based to the three-dimensional image) and etc. The large-scale image here refers to an image with a resolution ranging from I million×(multiplied by) J million to M hundred×(multiplied by) N hundred, where I, J, M and N are integers greater than 0.

The medical image data here can be acquired in a variety of ways, for example, the medical image data can be acquired from the upload from a doctor or a patient or a third party, or acquired by connecting to a data management system inside or outside the hospital (such as a hospital information system, an image archiving and communication system PACS applied in a hospital imaging department), or acquired by connecting to a specific data storage server (such as a medical image cloud).

Step 120, generating multi-scale decision sample data based on the medical image data.

In some embodiments, when generating the multi-scale decision sample data, the method for acquiring the decision sample data of each scale can be an existing technology or a technology to be developed in the future, the present disclosure will not be limited thereto. For example, zoom images of different scales can be first generated based on the medical image data, then the decision sample data can be selected from the zoom images randomly, according to a predetermined rule, or according to a manual input.

In a specific example, a non-effective pathological tissue area in the medical image data can be removed to obtain an effective pathological tissue area; then the multi-scale decision sample data is generated based on the effective pathological tissue area. The multi-scale decision sample data here may include at least one of: decision sample data observed at different observation scales or decision sample data observed at different resolutions.

Step 130, inputting the multi-scale decision sample data into a deep neural network model to obtain an auxiliary diagnosis data of the medical image.

In some embodiments, the deep neural network model may be obtained by training based on a consistency principle between data and an output result using multi-scale training sample data. The multi-scale training sample data may include at least one of: training sample data observed at different observation scales or training sample data observed at different resolutions, and these training sample data are medical image data with manually annotated data. For example, the multi-scale training sample data may include medical image data of an annotated health image and an annotated disease image, furthermore the medical image data of the annotated disease image may also be medical image data of annotated lesion area. The deep neural network model here may adopt a deep neural network model applicable to a medical image auxiliary diagnosis. Specifically, the deep neural network model may be determined according to a required to-be-achieved function of the medical image auxiliary diagnosis.

In some optional implementations of some embodiments, the deep neural network model nay include one or more of disease classification, disease area detection, or disease area segmentation. That is, the deep neural network model should achieve one or more of the following functions: disease classification, disease area detection, or disease area segmentation.

While achieving these functions, an identical deep neural network model may be used to achieve these functions, or these functions can be respectively achieved using a plurality of identical or different deep neural network models. For example, a deep neural network model may be used to achieve disease classification, and another deep neural network model identical to or different from the deep neural network model for achieving disease classification may be used to achieve disease area detection and disease area segmentation.

As an example, a deep neural network model can be used to achieve disease classification, for example, VGG16, ResNet, Inception, or 3D CNN can be used to achieve disease classification. VGG16 is a convolution deep neural network, and this structure has 13 convolution layers and 3 full link layers, which totally has 13+3=16 layers. ResNet does not decompose the original problem, but instead decomposes the deep neural network to reduce the complexity of a fitting function, a loss function is a function of the fitting function, so reducing the complexity of the fitting function is equivalent to reducing the complexity of the loss function. Inception is a convolution deep neural network proposed by Google which is deeper than VGG16. Inception uses convolution kernels of different sizes (for example, with mixed 1×1, 3×3, 5×5) to improve network width and adaptability, which may reduce network training parameters, improve generalization ability and accuracy. 3D CNN is a three-dimensional convolution deep neural network, which is mainly used for three-dimensional data training using three-dimensional convolution operation. The deep neural network model for data classification here can further rank the classified medical image data to obtain medical image data of different levels when classifying the medical image data.

As an example, a deep neural network model can be used to realize lesion area recognition. The deep neural network model can adopt one or a combination of multiple convolution deep neural networks applicable to lesion area detection, lesion area segmentation and lesion area classification, such as FCN, Mask-RCNN, MNC, U-NET, 3D CNN, or 3D U-NET. FCN is a full convolution deep neural network, and is mainly used for image segmentation, where dimension reduction is performed first for training and fitting, and then a dimension of the result is increased reversely to achieve pixel level segmentation of the image. Mask-RCNN is a multi-task convolution deep neural network for performing image classification, specific object detection and segmentation simultaneously. MNC is a multi-task deep neural network cascade, which is a multi-task convolution deep neural network for performing image target detection and segmentation. U-NET is a U-shaped convolution deep neural network, which is a convolution deep neural network for performing image segmentation, using similar techniques like FCN, combining shallow feature map with deep feature map to generate more accurate segmentation results, and it is named U-NET because its network structure is similar to U shape. 3D CNN is a three-dimensional convolution deep neural network, which is mainly used for three-dimensional data training by adopting three-dimensional convolution operation. 3D U-NET is a three-dimensional U-shaped convolution deep neural network, which is a three-dimensional convolution deep neural network for segmenting three-dimensional data, the principle thereof is similar to U-NET, using three-dimensional convolution network for performing three-dimensional data processing.

The auxiliary diagnosis data of the medical image can be obtained after the acquired medical image data is analyzed by the above trained neural network model.

In the method for analyzing a medical image according to an embodiment of the present disclosure, the medical image is analyzed and recognized based on the deep neural network model, wherein the deep neural network model is trained according to the consistency principle between data and an output result using multi-scale training sample data, thus the multi-scale lesion area detection, segmentation and decision are performed on the full-field pathological image, thereby accelerating the training time of the deep neural network model, improving the reliability and robustness of the deep neural network model effectively, and further improving the accuracy of the auxiliary diagnosis data of the medical image.

Figure 2:
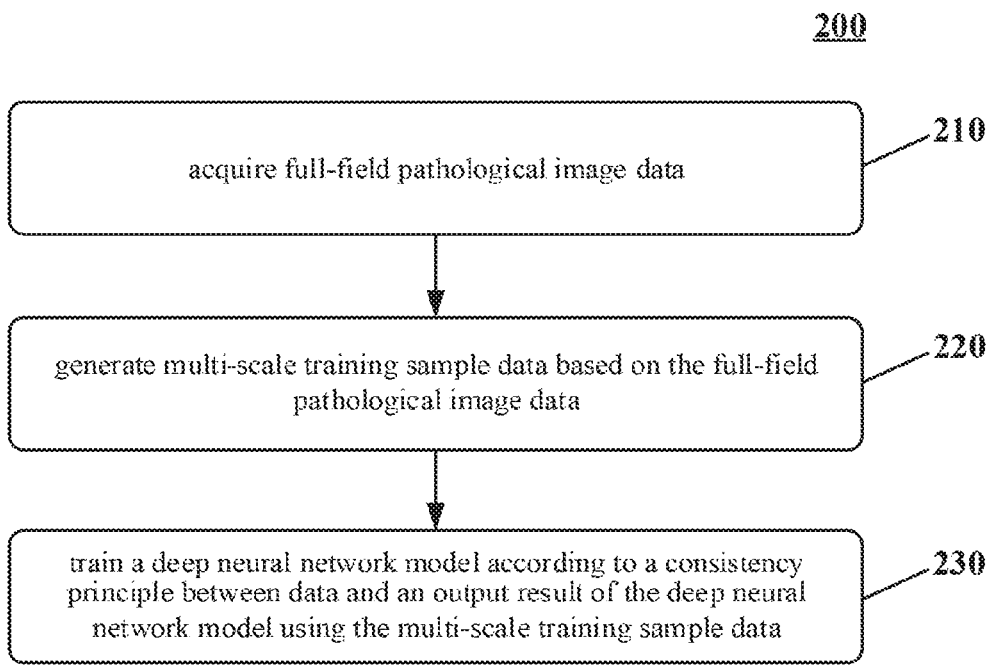
FIG. 2 is a schematic flowchart of an embodiment of a method for training a deep neural network model in FIG. 1 according to the present disclosure.

Further referring to FIG. 2, FIG. 2 shows a schematic flowchart of an embodiment of a method for training a deep neural network model in FIG. 1 according to some embodiments of the present disclosure.

As shown in FIG. 2, the method for training the deep neural network model 200 includes:

Step 210, acquiring full-field pathological image data.

In some embodiments, the full-field pathological image data refers to a whole-slide image (WSI). For example, the full-field pathological image data can be obtained by following steps: First glass slides are scanned slide by slide by a digital microscope or magnification system under a low magnification objective to acquire images, the microscope scanning platform automatically moves along the XY axis of the slide, and automatically focuses on the Z axis. Then, on the basis of the effective magnification of an optical amplifying device, high-resolution digital images are collected by a scanning control software using the program-controlled scanning, and an image compression and storage software automatically performs seamless stitching on the images, to generate a whole-slide image.

Step 220, generating multi-scale training sample data based on the full-field pathological image data.

In some embodiments, in order to simplify the complexity of subsequent processing, improve training efficiency and save computing resources, when selecting multi-scale training sample data, the multi-scale training sample data generated based on the full-field pathological image data can be considered.

When generating the multi-scale decision sample data, the method for acquiring the decision sample data of each scale can be the same as the one in the existing technology or the technology to be developed in the future, the present disclosure will not be limited thereto. For example, zoom images of different scales may be first generated for the medical image data, then the decision sample data can be selected from the zoom images randomly, according to a predetermined rule, or according to a manual input.

In a specific example, a non-effective pathological tissue area in the full-field pathological image data can be removed, to obtain an effective pathological tissue area; then the multi-scale training sample data is generated based on the effective pathological tissue area.

In order to determine a positional correspondence relationship between the multi-scale training sample data, the positional correspondence relationship between the multi-scale training sample data may be determined using a multi-scale alignment algorithm in the existing technology or technology to be developed in the future, the present disclosure will not be limited thereto.

When generating the multi-scale training sample data based on the full-field pathological image data, different multi-scale algorithms may be used to process the positive and negative samples of the full-field pathological image data to obtain the multi-scale training sample data; or the identical multi-scale algorithm may be used to process the positive and negative samples of the full-field pathological image data to obtain the multi-scale training sample data. The positive and negative samples here include a positive sample which contains a disease area annotated by a doctor, and a negative sample which does not contain a disease area annotated by a doctor and is a sample with a very healthy area.

Step 230, training a deep neural network model according to a consistency principle between data and an output result of the deep neural network model using the multi-scale training sample data.

In some embodiments, since a size of a lesion area in the multi-scale training sample data is irregular, and lesions may exist across multiple samples of different scales and sizes. Therefore, for a lesion area, training and testing may be performed at each scale; and the training and detection process can be overall accelerated based on the precondition of "when an identical lesion area is input into the deep neural network/networks trained by the training sample data of different scales, the output result should be consistent", and the accuracy of the overall network can be improved.

Here, in order to create a connection between training sample data of different scales more efficiently, first the connection between the training sample data of different scales in the multi-scale training sample data can be established by using topology or dynamic coding; then a deep neural network model is trained based on the connection between the training sample data of different scales.

In an optional example, when the multi-scale training sample data is generated based on the effective pathological tissue area, the deep neural network model is trained taking a lesion rather than an image as a unit, and neural networks of different scales are trained after finding pictures of the identical lesion at different scales, thus it is convenient to adjust parameters once mistakes occur, thereby improving the training effect and accuracy.

When training a deep neural network model, the deep neural network model can be trained jointly using the training sample data of different scales in the multi-scale training sample data which connect with each other to improve the training effect and accuracy; or the deep neural network model can be trained respectively using the training sample data of different scales in the multi-scale training sample data separately, and networks trained by training sample data of different scales are independent from each other.

When training the deep neural network model using the multi-scale training sample data, in order to balance the proportion of positive and negative samples and avoid the occurrence of over fitting phenomenon, sample data with a score lower than a predetermined threshold may be selected from the multi-scale training sample data for back propagation, to update parameters of the deep neural network model. In this way, a large amount of back propagation time may be saved, and the deep neural network model may learn inappropriate samples under the current decision result more effectively. Alternatively or additionally, sample data expired in training and/or detection may be selected from the multi-scale training sample data for Hard Example Mining, to update parameters of the deep neural network model, thus two kinds of training sample data very similar to each other in appearance can be distinguished, and further the deep neural network model can learn inappropriate samples under the current decision result more effectively.

In the method for training a deep neural network model according to an embodiment of the present disclosure, a deep neural network model is trained according to a consistency principle between data and an output result of the deep neural network model using the multi-scale training sample data, thereby improving the reliability and robustness of the model effectively, and also improving the accuracy of diagnosis decision. In some embodiments, it may also greatly accelerate the training time by using dynamic coding, block topological relations, back propagation and hard example mining, thereby further improving the reliability and robustness of the model, and improving the accuracy of diagnosis decision.

An application scenario of the method for analyzing a medical image according to an embodiment of the present disclosure is described in conjunction with FIG. 3 below.

Figure 3:
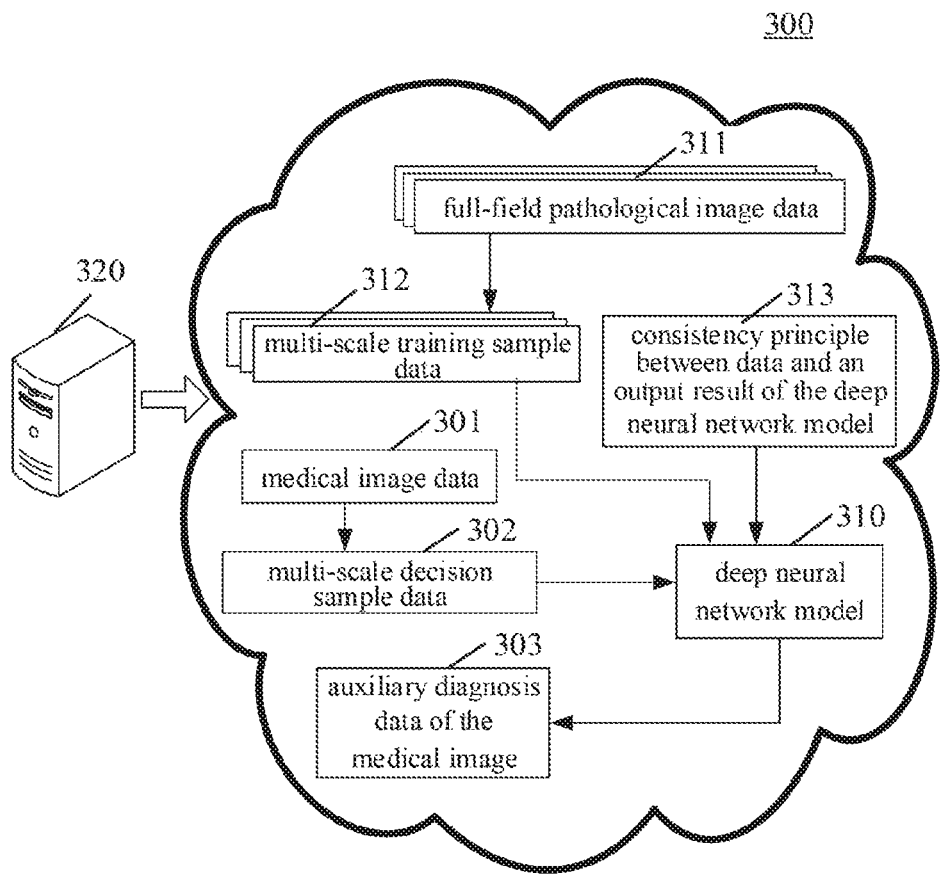
FIG. 3 is a flowchart of an application scenario of the method for analyzing a medical image according to an embodiment of the present disclosure.

As shown in FIG. 3, FIG. 3 shows a flowchart of an application scenario of the method for analyzing a medical image according to an embodiment of the present disclosure.

In FIG. 3, the method 300 for analyzing a medical image is applied in an electronic device 320. For the currently acquired medical image data 301, multi-scale decision sample data 302 may be generated based on the medical image data 301; then the multi-scale decision sample data 302 is input into a pre-trained deep neural network model 310 to thereby obtain an auxiliary diagnosis data 303 of the medical image.

The deep neural network model 310 is trained by the following steps: first, full-field pathological image data 311 is acquired; next, multi-scale training sample data 312 is generated based on the full-field pathological image data 311; finally a deep neural network model 310 is trained according to a consistency principle 313 between data and an output result of the deep neural network model using the multi-scale training sample data 312.

The method for analyzing a medical image according to the above application scenario of the present disclosure can improve the training speed of the deep neural network, and improve the accuracy and precision of the analysis results. It should be understood by those skilled in the art that the above application scenario is only a description of the application scenario of an embodiment of the present disclosure, and does not represent a limitation to the present disclosure. For example, the present disclosure can also optimize the deep neural network model based on the sample data whose score is lower than the predetermined threshold and/or sample data expired in training and/or detection, so as to further enhance the efficiency and accuracy of disease diagnosis.

Figure 4:
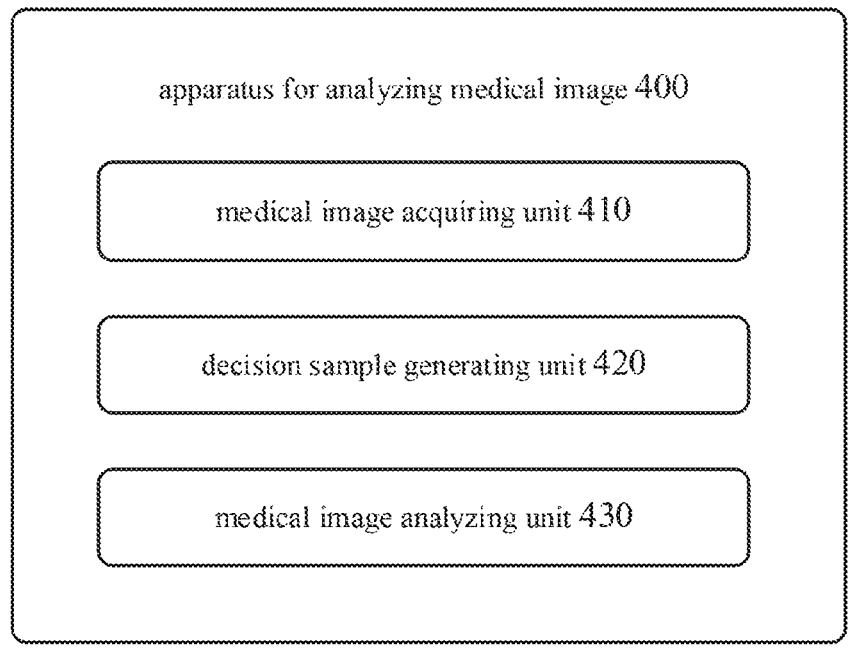
FIG. 4 is a schematic structural diagram of an embodiment of an apparatus for analyzing a medical image according to the present disclosure.

Further referring to FIG. 4, as an implementation of the above method, some embodiments of the present disclosure provide an embodiment of an apparatus for analyzing a medical image, some embodiments of the apparatus for analyzing a medical image corresponds to the embodiments of the method for analyzing a medical image shown in FIGS. 1 to 3. The operations and features described above for the method for analyzing a medical image in FIGS. 1 to 3 are equally applicable to the apparatus 400 for analyzing a medical image and units contained therein, so a further description thereof will be omitted in this context.

As shown in FIG. 4, the apparatus 400 configured to analyze a medical image includes: a medical image acquiring unit 410, configured to acquire medical image data; a decision sample generating unit 420, configured to generate multi-scale decision sample data based on the medical image data; a medical image analyzing unit 430, configured to input the multi-scale decision sample data into a deep neural network model to obtain an auxiliary diagnosis data of the medical image, the deep neural network model is trained according to a consistency principle between multi-scale training sample data and a output result of the deep neural network model.

In some optional implementations of the present embodiment (not shown in the figure), the deep neural network model in the medical image analyzing unit is trained through the following units: a pathological image acquiring unit, configured to acquire full-field pathological image data; a training sample generating unit, configured to generate multi-scale training sample data based on the full-field pathological image data; a neural network training unit, configured to train the deep neural network model according to a consistency principle between data and an output result of the deep neural network model using the multi-scale training sample data.

In some optional implementations of the present embodiment (not shown in the figure), the sample data generating unit includes: a pathological area determining unit, configured to remove a non-effective pathological tissue area in the full-field pathological image data to obtain an effective pathological tissue area; a lesion sample generating unit, configured to generate the multi-scale training sample data based on the effective pathological tissue area.

In some optional implementations of the present embodiment, the sample data generating unit is further configured to: determine a positional correspondence relationship between the multi-scale training sample data using a multi-scale alignment algorithm.

In some optional implementations of the present embodiment, the sample data generating unit is further configured to: respectively train the deep neural network model using training sample data of different scales in the multi-scale training sample data; or jointly train the deep neural network model using the training sample data of different scales in the multi-scale training sample data.

In some optional implementations of the present embodiment, the sample data generating unit is further configured to: establish a connection between the training sample data of different scales in the multi-scale training sample data using topology or dynamic coding; and train the deep neural network model based on the connection between the training sample data of different scales.

In some optional implementations of the present embodiment, the neural network training unit is further configured to: select sample data with a score lower than a predetermined threshold from the multi-scale training sample data for back propagation, to update parameters of the deep neural network model; and/or select sample data expired in training and/or detection from the multi-scale training sample data for hard example mining, to update parameters of the deep neural network model.

In some optional implementations of the present embodiment, the deep neural network model in the neural network training unit includes one or more of disease classification, disease area detection, or disease area segmentation.

The present disclosure further provides an embodiment of a device, including: one or more processors; and a storage apparatus, configured to store one or more programs. The one or more programs, when executed by the one or more processors, cause the one or more processors to implement the methods for analyzing medical image described in any one of the above embodiments.

The present disclosure further provides an embodiment of a computer readable storage medium, storing a computer program thereon. The computer program, when executed by a processor, implements the methods for analyzing medical image described in any one of the above embodiments.

Figure 5:
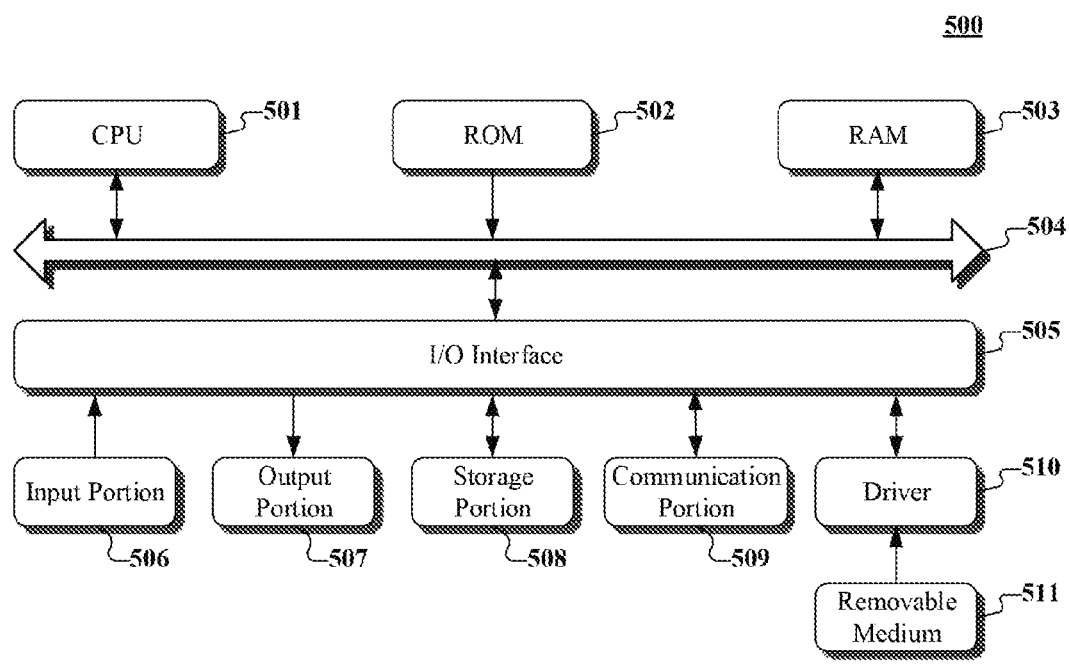
FIG. 5 is a schematic structural diagram of a computer system of a terminal device or a server applicable to implementing an embodiment of the present disclosure.

Referring to FIG. 5 below, FIG. 5 shows a schematic structural diagram of a computer system 500 of a terminal device or a server applicable to implementing some embodiments of the present disclosure. The terminal device shown in FIG. 5 is merely an example, and should not impose any limitation on the function and usage range of the embodiments of the present disclosure.

As shown in FIG. 5, the computer system 500 includes a central processing unit (CPU) 501, which may execute various appropriate actions and processes in accordance with a program stored in a read-only memory (ROM) 502 or a program loaded into a random access memory (RAM) 503 from a storage portion 508. The RAM 503 also stores various programs and data required by operations of the system 500. The CPU 501, the ROM 502 and the RAM 503 are connected to each other through a bus 504. An input/output (I/O) interface 505 is also connected to the bus 504.

The following components are connected to the I/O interface 505: an input portion 506 including a keyboard, a mouse etc.; an output portion 507 comprising a cathode ray tube (CRT), a liquid crystal display device (LCD), a speaker etc.; a storage portion 508 including a hard disk and the like; and a communication portion 509 comprising a network interface card, such as a LAN card and a modem. The communication portion 509 performs communication processes via a network, such as the Internet. A driver 510 is also connected to the I/O interface 505 as required. A removable medium 511, such as a magnetic disk, an optical disk, a magneto-optical disk, and a semiconductor memory, may be installed on the driver 510, to facilitate the retrieval of a computer program from the removable medium 511, and the installation thereof on the storage portion 508 as needed.

In particular, according to some embodiments of the present disclosure, the process described above with reference to the flow chart may be implemented in a computer software program. For example, an embodiment of the present disclosure includes a computer program product, which comprises a computer program that is tangibly embedded in a machine-readable medium. The computer program comprises program codes for executing the method as illustrated in the flow chart. In such an embodiment, the computer program may be downloaded and installed from a network via the communication portion 509, and/or may be installed from the removable media 511. The computer program, when executed by the central processing unit (CPU) 501, implements the above mentioned functionalities as defined by the methods of the present disclosure.

It should be noted that the computer readable medium in the present disclosure may be computer readable signal medium or computer readable storage medium or any combination of the above two. An example of the computer readable storage medium may include, but not limited to: electric, magnetic, optical, electromagnetic, infrared, or semiconductor systems, apparatus, elements, or a combination any of the above. A more specific example of the computer readable storage medium may include but is not limited to: electrical connection with one or more wire, a portable computer disk, a hard disk, a random access memory (RAM), a read only memory (ROM), an erasable programmable read only memory (EPROM or flash memory), a fibre, a portable compact disk read only memory (CD-ROM), an optical memory, a magnet memory or any suitable combination of the above. In the present disclosure, the computer readable storage medium may be any physical medium containing or storing programs which can be used by a command execution system, apparatus or element or incorporated thereto. In the present disclosure, the computer readable signal medium may include data signal in the base band or propagating as parts of a carrier, in which computer readable program codes are carried. The propagating signal may take various forms, including but not limited to: an electromagnetic signal, an optical signal or any suitable combination of the above. The signal medium that can be read by computer may be any computer readable medium except for the computer readable storage medium. The computer readable medium is capable of transmitting, propagating or transferring programs for use by, or used in combination with, a command execution system, apparatus or element. The program codes contained on the computer readable medium may be transmitted with any suitable medium including but not limited to: wireless, wired, optical cable, RF medium etc., or any suitable combination of the above.

The flow charts and block diagrams in the accompanying drawings illustrate architectures, functions and operations that may be implemented according to the systems, methods and computer program products of the various embodiments of the present disclosure. In this regard, each of the blocks in the flow charts or block diagrams may represent a module, a program segment, or a code portion, said module, program segment, or code portion comprising one or more executable instructions for implementing specified logic functions. It should also be noted that, in some alternative implementations, the functions denoted by the blocks may occur in a sequence different from the sequences shown in the figures. For example, any two blocks presented in succession may be executed, substantially in parallel, or they may sometimes be in a reverse sequence, depending on the function involved. It should also be noted that each block in the block diagrams and/or flow charts as well as a combination of blocks may be implemented using a dedicated hardware-based system executing specified functions or operations, or by a combination of a dedicated hardware and computer instructions.

The units or modules involved in the embodiments of the present disclosure may be implemented by means of software or hardware. The described units or modules may also be provided in a processor, for example, described as: a processor, comprising a medical image acquiring unit, a sample decision generating unit, and a medical image analyzing unit, where the names of these units or modules do not in some cases constitute a limitation to such units or modules themselves. For example, the medical image acquiring unit may also be described as "a unit for acquiring medical image.

In another aspect, some embodiments of the present disclosure further provide a non-volatile computer storage medium. The non-volatile computer storage medium may be the non-volatile computer storage medium included in the apparatus in the above described embodiments, or a stand-alone non-volatile computer storage medium not assembled into the terminals. The non-volatile computer storage medium stores one or more programs. The one or more programs, when executed by a device, cause the device to: acquire medical image data; generate multi-scale decision sample data based on the medical image data; and input the multi-scale decision sample data into a deep neural network model to obtain diagnosis data of the medical image, wherein the deep neural network model is trained according to a consistency principle between data and an output result using multi-scale training sample data.

The above description only provides an explanation of the preferred embodiments of the present disclosure and the technical principles used. It should be appreciated by those skilled in the art that the inventive scope of the present disclosure is not limited to the technical solutions formed by the particular combinations of the above-described technical features. The inventive scope should also cover other technical solutions formed by any combinations of the above-described technical features or equivalent features thereof without departing from the concept of the disclosure. Technical schemes formed by the above-described features being interchanged with, but not limited to, technical features with similar functions disclosed in the present disclosure are examples.

What is claimed is:
1. A method for analyzing a medical image, the method comprising:
 acquiring medical image data;
 generating multi-scale decision sample data based on the medical image data; and
 inputting the multi-scale decision sample data into a deep neural network model to obtain auxiliary diagnosis data of the medical image, wherein the deep neural network model is trained using multi-scale training sample data according to a consistency principle between the multi-scale training sample data and an output result, wherein the deep neural network model is trained by:
 acquiring full-field pathological image data;
 generating the multi-scale training sample data based on the full-field pathological image data; and training the deep neural network model according to a consistency principle between the multi-scale training sample data and the output result of the deep neural network model using the multi-scale training sample data, wherein the generating the multi-scale training sample data based on the full-field pathological image data comprises:
removing a non-effective pathological tissue area in the full-field pathological image data to obtain an effective pathological tissue area; and
generating the multi-scale training sample data based on the effective pathological tissue area, and wherein the method is performed by at least one processor.

2. The method according to claim 1, wherein the generating the multi-scale training sample data based on the full-field pathological image data comprises:
determining a positional correspondence relationship between the multi-scale training sample data using a multi-scale alignment algorithm.

3. The method according to claim 1, wherein the training the deep neural network model using the multi-scale training sample data comprises:
training the deep neural network model respectively using training sample data of different scales in the multi-scale training sample data; or
training the deep neural network model jointly using the training sample data of different scales in the multi-scale training sample data.

4. The method according to claim 1, wherein the training the deep neural network model using the multi-scale training sample data comprises:
establishing a connection between training sample data of different scales in the multi-scale training sample data using topology or dynamic coding; and
training the deep neural network model based on the connection between the training sample data of different scales.

5. The method according to claim 1, wherein the training the deep neural network model using the multi-scale training sample data comprises at least one of:
selecting sample data with a score lower than a predetermined threshold from the multi-scale training sample data for back propagation, to update parameters of the deep neural network model; or
selecting sample data expired in at least one of training or detection from the multi-scale training sample data for hard example mining, to update parameters of the deep neural network model.

6. The method according to claim 1, wherein the deep neural network model comprises one or more of disease classification, disease area detection, or disease area segmentation.

7. An apparatus for analyzing a medical image, the apparatus comprising:
at least one processor; and
a memory storing instructions, the instructions when executed by the at least one processor, cause the at least one processor to perform operations, the operations comprising:
acquiring medical image data;
generating multi-scale decision sample data based on the medical image data; and
inputting the multi-scale decision sample data into a deep neural network model to obtain an auxiliary diagnosis data of the medical image, wherein the deep neural network model is trained using multi-scale training sample data according to a consistency principle between the multi-scale training sample data and an output result, wherein the deep neural network model is trained by:
acquiring full-field pathological image data;
generating the multi-scale training sample data based on the full-field pathological image data; and
training the deep neural network model according to a consistency principle between the multi-scale training sample data and the output result of the deep neural network model using the multi-scale training sample data, and wherein the generating the multi-scale training sample data based on the full-field pathological image data comprises:
removing a non-effective pathological tissue area in the full-field pathological image data to obtain an effective pathological tissue area; and
generating the multi-scale training sample data based on the effective pathological tissue area.

8. The apparatus according to claim 7, wherein the generating the multi-scale training sample data based on the full-field pathological image data comprises:
determining a positional correspondence relationship between the multi-scale training sample data using a multi-scale alignment algorithm.

9. The apparatus according to claim 7, wherein the training the deep neural network model using the multi-scale training sample data comprises:
training the deep neural network model respectively using training sample data of different scales in the multi-scale training sample data; or
training the deep neural network model jointly using the training sample data of different scales in the multi-scale training sample data.

10. The apparatus according to claim 7, wherein the training the deep neural network model using the multi-scale training sample data further comprises:
establishing a connection between training sample data of different scales in the multi-scale training sample data using topology or dynamic coding; and
training the deep neural network model based on the connection between the training sample data of different scales.

11. The apparatus according to claim 7, wherein the training the deep neural network model using the multi-scale training sample data comprises at least one of:
selecting sample data with a score lower than a predetermined threshold from the multi-scale training sample data for back propagation, to update parameters of the deep neural network model; or
selecting sample data expired in at least one of training or detection from the multi-scale training sample data for hard example mining, to update parameters of the deep neural network model.

12. The apparatus according to claim 7, wherein the deep neural network model comprises one or more of disease classification, disease area detection, or disease area segmentation.

13. A non-transitory computer readable storage medium, storing a computer program thereon, wherein the computer program, when executed by a processor, causes the processor to perform operations, the operations comprising:
acquiring medical image data;
generating multi-scale decision sample data based on the medical image data; and inputting the multi-scale decision sample data into a deep neural network model to obtain auxiliary diagnosis data of the medical image, wherein the deep neural network model is trained using multi-scale training sample data according to a consistency principle between the multi-scale training sample data and an output result, wherein the deep neural network model is trained by:

acquiring full-field pathological image data;

generating the multi-scale training sample data based on the full-field pathological image data; and training the deep neural network model according to a consistency principle between the multi-scale training sample data and an output result of the deep neural network model using the multi-scale training sample data, and wherein the generating the multi-scale training sample data based on the full-field pathological image data comprises:

removing a non-effective pathological tissue area in the full-field pathological image data to obtain an effective pathological tissue area; and generating the multi-scale training sample data based on the effective pathological tissue area.

\* \* \* \* \*